(12) United States Patent
Rivolta et al.

(10) Patent No.: US 12,247,849 B2
(45) Date of Patent: Mar. 11, 2025

(54) ENHANCED HUMAN ACTIVITY RECOGNITION (71) Applicant: STMICROELECTRONICS S.r.l., Agrate Brianza (IT)

(72) Inventors: Stefano Paolo Rivolta, Desio (IT); Roberto Mura, Milan (IT)

(73) Assignee: STMICROELECTRONICS S.r.l., Agrate Brianza (IT)

(*) Notice: Subject to any disclaimer, the term of this patent is extended or adjusted under 35 U.S.C. 154(b) by 376 days.

(21) Appl. No.: 17/459,781

(22) Filed: Aug. 27, 2021

(65) Prior Publication Data
US 2023/0075382 A1 Mar. 9, 2023

(51) Int. Cl.
G01D 21/02 (2006.01)
A61B 5/11 (2006.01)
A61B 5/24 (2021.01)
G01P 15/00 (2006.01)
G01R 29/12 (2006.01)

(52) U.S. Cl.
CPC ............ *G01D 21/02* (2013.01); *A61B 5/1118* (2013.01); *A61B 5/2415* (2021.01); *G01P 15/00* (2013.01); *G01R 29/12* (2013.01); *A61B 2562/0219* (2013.01)

(58) Field of Classification Search
CPC ....... A61B 5/2415; A61B 5/24; A61B 5/1118; A61B 2562/0219; A61B 5/1123; A61B 5/7264; A61B 5/0531; A61B 5/112; A61B 5/681; G01D 21/02; G06F 1/3231; G06F 1/1694; G06F 18/24; G06F 2218/08; G06F 2218/14; G06N 20/00; G06N 7/01; G06N 5/02; G01P 15/00; G01P 15/14; G01P 15/08; G01R 29/12; G06V 40/25; H04M 1/72454; H04W 4/38
See application file for complete search history.

(56) References Cited

U.S. PATENT DOCUMENTS 10,141,929 B2 * 11/2018 Rakova ................... G06N 7/01
10,540,597 B1 * 1/2020 Tilton ..................... G10L 25/03
10,605,595 B2    3/2020 Martensson et al.
(Continued)

FOREIGN PATENT DOCUMENTS

CN         108236469 A    7/2018
EP           2980609 A1   2/2016
(Continued)

OTHER PUBLICATIONS

Wilmsdorff et al., "An experimental overview on electric field sensing," *Journal of Ambient Intelligence and Humanized Computing* 10:813-824, 2019.
(Continued)

*Primary Examiner* — Daniel R Miller
*Assistant Examiner* — Eric Sebastian Von Wald
(74) *Attorney, Agent, or Firm* — Seed IP Law Group LLP (57) ABSTRACT The present disclosure is directed to a device with enhanced human activity recognition. The device detects a human activity using one more motion sensors, and enhances the detected human activity depending on whether the device is in an indoor environment or an outdoor environment. The device utilizes one or more electrostatic charge sensors to determine whether the device is in an indoor environment or an outdoor environment.

18 Claims, 3 Drawing Sheets

(56) References Cited

U.S. PATENT DOCUMENTS

| | | | |
|---|---|---|---|
| 10,943,602 B2 | 3/2021 | Chowdhary et al. | |
| 11,257,198 B1 | 2/2022 | Holub et al. | |
| 2003/0001582 A1* | 1/2003 | Kraz | H01L 21/67253 |
| | | | 324/457 |
| 2007/0100666 A1 | 5/2007 | Stivoric et al. | |
| 2013/0159237 A1* | 6/2013 | Nath | H04W 52/0209 |
| | | | 706/47 |
| 2014/0232516 A1 | 8/2014 | Stivoric et al. | |
| 2014/0358473 A1* | 12/2014 | Goel | A61B 5/1118 |
| | | | 702/141 |
| 2015/0097731 A1* | 4/2015 | Russell | G01S 5/012 |
| | | | 342/450 |
| 2016/0296144 A1* | 10/2016 | Gaddam | G01P 15/00 |
| 2016/0305776 A1* | 10/2016 | Mårtensson | A61B 5/1118 |
| 2016/0342781 A1 | 11/2016 | Jeon | |
| 2018/0096256 A1* | 4/2018 | Chowdhary | G06F 16/2455 |
| 2019/0038184 A1 | 2/2019 | Narasimhan et al. | |
| 2020/0382613 A1* | 12/2020 | Sundstrom | G06F 1/1698 |
| 2021/0081032 A1 | 3/2021 | Passaniti et al. | |
| 2021/0232227 A1 | 7/2021 | Passaniti et al. | |
| 2021/0285773 A1 | 9/2021 | Alessi et al. | |
| 2023/0035435 A1* | 2/2023 | Thamma | G01R 29/14 |
| 2023/0050034 A1* | 2/2023 | Ben-Elazar | G06N 20/00 |
| 2023/0065695 A1* | 3/2023 | Singleton | G06F 9/451 |

FOREIGN PATENT DOCUMENTS

| | | | |
|---|---|---|---|
| KR | 2001077112 A | * | 8/2001 |
| KR | 1020110061750 A | | 6/2011 |
| WO | 2016166613 A1 | | 10/2016 |
| WO | WO-2019176762 A1 | * | 9/2019 |
| WO | WO 2020196993 A1 | | 10/2020 |

OTHER PUBLICATIONS

Cohn, G. et al., "An Ultra-Low-Power Human Body Motion Sensor Using Static Electric Field Sensing," *Proceedings of the 2012 ACM Conference on Ubiquitous Computing*, Sep. 2012, 5 pages.

Fu et al., "Sensing Technology for Human Activity Recognition: A Comprehensive Survey," *IEEE Access, 2020*, 8, pp. 83791-83820.

Lima et al., "Human Activity Recognition Using Inertial Sensors in a Smartphone: An 2 Overview," *Sensors, 2019*, 19(3213):1-28.

Radivojevic et al., "Human Activity Recognition based on Machine Learning 3 Classification of Smartwatch Accelerometer Dataset," *FME Transactions, 2021*, 49(1):225-232.

Khusainov, R.; Azzi, D.; Achumba, I.E.; Bersch, S.D. Real-Time Human Ambulation, Activity, and Physiological Monitoring: Taxonomy of Issues, Techniques, Applications, Challenges and Limitations. Sensors 2013, 13, 12852-12902. https://doi.org/10.3390/S131012852 (Year: 2013).

Lutz, J.; Memmert, D.; Raabe, D.; Dornberger, R.; Donath, L. Wearables for Integrative Performance and Tactic Analyses: Opportunities, Challenges, and Future Directions. Int. J. Environ. Res. Public Health 2020, 17, 59. https://doi.org/10.3390/ ijerph 17010059 (Year: 2019).

Del Rosario, M.B.; Redmond, S.J.; Lovell, N.H. Tracking the Evolution of Smartphone Sensing for Monitoring Human Movement. Sensors 2015, 15, 18901-18933. https://doi.org/10.3390/s150818901 (Year: 2015).

* cited by examiner

ENHANCED HUMAN ACTIVITY RECOGNITION

BACKGROUND

Technical Field

The present disclosure is directed to a system and method for detecting human activity.

Description of the Related Art

Human activity recognition is commonly used in portable devices, such as smart phones, wireless headphones, and smart wearable devices, to detect and track activities of a user. For example, human activity recognition may be used to detect whether a user is stationary, walking, travelling in a vehicle, or performing other types of activities. Devices typically utilize motion sensors to perform human activity recognition. Many devices, for instance, include accelerometers and gyroscopes, and detect a user's activity based on acceleration and angular velocity measurements of the device.

It is desirable for device manufacturers to perform human activity recognition with higher class resolution in order to detect additional types of activities. For example, some devices offer solutions with context awareness in addition to human activity recognition. These types of devices, for example, are capable of distinguishing between indoor or outdoor environments, and may perform specific processes, such as indoor and outdoor navigation.

Devices with context awareness typically distinguish between indoor and outdoor environments by utilizing microphones to detect environmental noise, and audio classification methods to classify the environmental noise as an indoor or outdoor environment. Unfortunately, the use of microphones consumes large amounts of power. In addition, audio classification methods are sensitive to where the device is being carried, as a microphone signal will differ between the device being carried in a user's hand or a user's pocket. Consequently, current audio classification methods employ extensive dataset training and complex deep learning algorithms. Due to the high power and processing demands of current context awareness implementations, context awareness are mostly limited to premium devices. Many low cost, budget devices do not have context awareness capabilities.

BRIEF SUMMARY

The present disclosure is directed to a device with enhanced human activity recognition. The device detects a human activity with one or more motion sensors, determines whether the device is in an indoor environment or an outdoor environment, and enhances the detected human activity depending on whether the device is in an indoor environment or an outdoor environment. For example, the device may validate the detected human activity or refine the detected human activity to a new activity depending on whether the device is in an indoor environment or an outdoor environment.

In contrast to audio-based solutions that utilize microphones to detect an indoor and outdoor environment, the device disclosed herein utilizes one or more electrostatic charge sensors to determine whether the device is in an indoor environment or an outdoor environment. The device disclosed herein consumes significantly less power and has faster processing times compared to devices with audio-based solutions.

BRIEF DESCRIPTION OF THE SEVERAL VIEWS OF THE DRAWINGS

In the drawings, identical reference numbers identify similar features or elements. The size and relative positions of features in the drawings are not necessarily drawn to scale.

DETAILED DESCRIPTION

In the following description, certain specific details are set forth in order to provide a thorough understanding of various aspects of the disclosed subject matter. However, the disclosed subject matter may be practiced without these specific details. In some instances, well-known machine learning techniques and structures and methods of manufacturing electronic devices and sensors have not been described in detail to avoid obscuring the descriptions of other aspects of the present disclosure.

Unless the context requires otherwise, throughout the specification and claims that follow, the word "comprise" and variations thereof, such as "comprises" and "comprising," are to be construed in an open, inclusive sense, that is, as "including, but not limited to."

Reference throughout the specification to "one embodiment" or "an embodiment" means that a particular feature, structure, or characteristic described in connection with the embodiment is included in at least one embodiment. Thus, the appearance of the phrases "in one embodiment" or "in an embodiment" in various places throughout the specification are not necessarily all referring to the same aspect. Furthermore, the particular features, structures, or characteristics may be combined in any suitable manner in one or more aspects of the present disclosure.

As discussed above, some devices offer solutions with context awareness in addition to human activity recognition. Generally, these devices distinguish between indoor and outdoor environments using audio-based solutions. For example, the device detects environmental noise with microphones, and classifies the environmental noise as an indoor or outdoor environment with audio classification methods. The use of microphones and audio classification methods consumes large amounts of power and has high processing demands.

The present disclosure is directed to a device with enhanced human activity recognition. The device utilizes one or more motion sensors to detect human activities, such as remaining stationary, walking, cycling, and driving; and utilizes one or more electrostatic charge sensors to detect whether the device is in an indoor or outdoor environment. The detected indoor or outdoor environment is then used in conjunction with the detected human activity in order to validate detected human activities and detect additional classes of activities.

Figure 1:
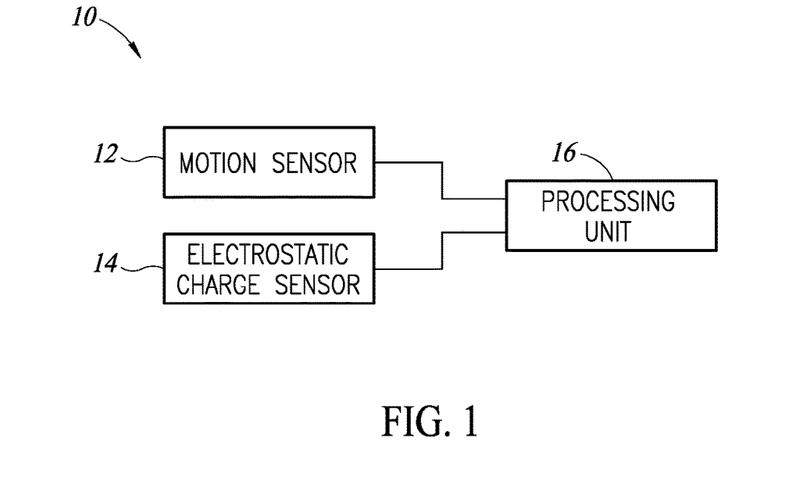
FIG. 1 is a block diagram of a device according to an embodiment disclosed herein.

FIG. 1 is a block diagram of a device 10 according to an embodiment disclosed herein. The device 10 is an electronic device that performs human activity recognition. For example, the device 10 may be a smart watch, a fitness tracking device, wireless headphones, a laptop computer, a tablet, or a cellular phone. The device includes a motion sensor 12, an electrostatic charge sensor 14, and a processing unit 16.

The motion sensor 12 is configured to measure a motion of the device 10, and generate a motion measurement that indicates the measured motion. In one embodiment, the motion measurement is in the form of an electrical signal (e.g., voltage or current signal) that is proportional to the measured motion.

The motion sensor 12 may be any type of sensor that detects movement of the device 10. For example, the motion sensor 12 may be an accelerometer that measures acceleration along at least one axis (e.g., a 3-axis accelerometer that measures acceleration along three different axes), or a gyroscope that measures angular velocity along at least one axis (e.g., a 3-axis gyroscope that measures angular velocity along three different axes).

Although a single motion sensor 12 is shown in FIG. 1, the device 10 may include any number of motion sensors. For instance, the device 10 may include a first motion sensor that is an accelerometer, and a second motion sensor that is a gyroscope.

In one embodiment, the motion sensor 12 is a combination sensor that includes both an accelerometer and a gyroscope, where the motion sensor 12 measures both acceleration and angular velocity. Operation of the motion sensor 12 will be discussed in further detail below.

The electrostatic charge sensor 14 is configured to measure an electrostatic charge of a surrounding environment, and generate an electrostatic charge measurement that indicates the measured electrostatic charge. In one embodiment, the electrostatic charge measurement is in the form of an electrical signal (e.g., voltage or current signal) that is proportional to the measured electrostatic charge.

Figure 2:
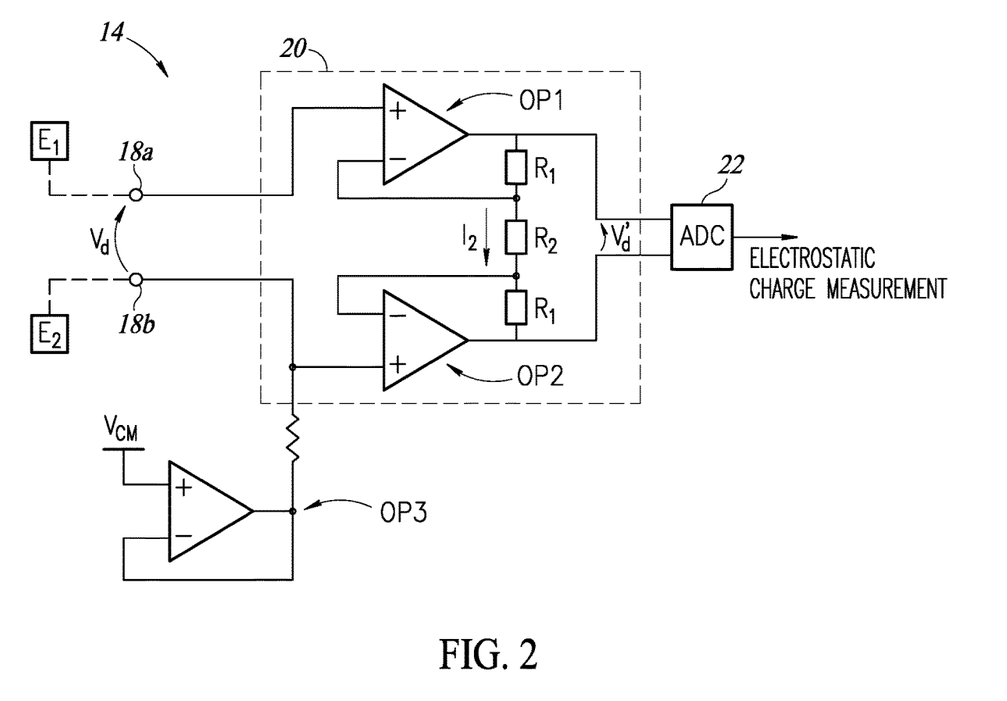
FIG. 2 is a diagram of an electrostatic charge sensor according to an embodiment disclosed herein.

The electrostatic charge sensor 14 includes one or more electrodes that detect electrostatic charge in a surrounding environment, and electrical components (e.g., resistors, capacitors, amplifiers, etc.) that measure the electrostatic charge detected by the single electrode. FIG. 2 is a diagram of the electrostatic charge sensor 14 according to an embodiment disclosed herein.

The electrostatic charge sensor 14 includes a pair of input terminals 18a, 18b, coupled to input electrodes $E_1$, $E_2$, respectively. Each of the electrodes $E_1$, $E_2$ is made of conductive material and, in one embodiment, coated with an insulating layer.

The geometry of the electrodes $E_1$, $E_2$ determines the sensitivity and directivity of the electrostatic charge sensor 14. The sensitivity is proportional to the surface area of the electrodes $E_1$, $E_2$. The shape of the electrodes $E_1$, $E_2$ and their positioning in space affects the directivity of the electrostatic charge sensor 14. In one embodiment, the electrodes $E_1$, $E_2$ are square in shape, with sides equal to about 2-10 cm (e.g., 5 cm).

In one embodiment, the electrodes $E_1$, $E_2$ are positioned inside of the device 10. In another embodiment, the electrodes $E_1$, $E_2$ are positioned on one or more exposed surfaces of the device 10 such that the electrodes $E_1$, $E_2$ are exposed to a surrounding environment. For example, the electrodes $E_1$, $E_2$ may be positioned on different side surfaces of the device 10.

The pair of input terminals 18a, 18b receive, from the respective electrodes $E_1$, $E_2$, an input voltage $V_d$. (a differential signal), and supply the input voltage $V_d$ to an instrumentation amplifier 20. As will be discussed in further detail below, a presence of an indoor alternating current (AC) power line generates a variation of electrostatic charge which, in turn, after having been detected by the electrodes $E_1$, $E_2$, generates the input voltage $V_d$.

The instrumentation amplifier 20 includes operational amplifiers OP1, OP2 and a biasing stage (buffer) OP3. The biasing stage OP3 biases the instrumentation amplifier 20 to a common mode voltage $V_{CM}$.

An inverting terminal of the amplifier OP1 is electrically connected to an inverting terminal of the amplifier OP2 through a resistor $R_2$ across which there is a voltage equal to the input voltage $V_d$. Therefore, a current equal to $I_2=V_d/R_2$ will flow through this resistor $R_2$. The current $I_2$ does not come from the input terminals of the operational amplifiers OP1, OP2, and, therefore, runs through two resistors $R_1$ connected between the outputs of the operational amplifiers OP1, OP2, in series with the resistor $R_2$. The current $I_2$, which runs through the series of the three resistors $R_1$-$R_2$-$R_1$, produces a differential output voltage $V_d'$, which is given by $V_d'=(2R_1+R_2)I_2=(2R_1+R_2)V_d/R_2$. The overall gain of the circuit of FIG. 2 is $Ad=V_d'/V_d=(2R_1+R_2)/R_2=1+2R_1/R_2$. The differential gain depends on the value of the resistor $R_2$ and may therefore be modified by acting on the resistor $R_2$.

The differential output voltage $V_d'$, therefore being proportional to the potential $V_d$ between the input terminals 18a, 18b, is input to an analog-to-digital converter (ADC) 22, which outputs a charge variation signal. The charge variation signal is, for example, a high-resolution digital stream (e.g., 16 bits or 24 bits). The charge variation signal is an electrostatic charge measurement of an electrostatic charge in a surrounding environment.

In another embodiment, the instrumentation amplifier 20 is omitted, so that the ADC 22 receives the differential output voltage $V_d$ between the electrodes $E_1$, $E_2$ and samples the differential output voltage $V_d$ directly. In another embodiment, the ADC 22 is omitted, and the charge variation signal is the differential output voltage $V_d$.

In the embodiment shown in FIG. 2, the electrostatic charge sensor 14 includes two electrodes. However, the electrostatic charge sensor 14 may include any number of electrodes. In one embodiment, the electrostatic charge sensor 14 includes a single electrode that detects electrostatic charge in a surrounding environment, and electrical components (e.g., resistors, capacitors, amplifiers, etc.) that measure the electrostatic charge detected by the single electrode.

Although a single electrostatic charge sensor 14 is shown in FIG. 1, the device 10 may include any number of electrostatic charge sensors. For example, the device 10 may include a first electrostatic charge sensor having two electrodes, and a second electrostatic charge sensor having another two electrodes.

Returning to FIG. 1, the processing unit 16 is communicatively coupled to the motion sensor 12 and the electrostatic charge sensor 14. The processing unit 16 is configured to receive motion measurements from the motion sensor 12 and electrostatic charge measurements from the electrostatic charge sensor 14, and detect or recognize human activity based on the motion measurements and electrostatic charge measurements. The processing unit 16 may be a processor, controller, signal processor, or any other type of processing unit.

Figure 3:
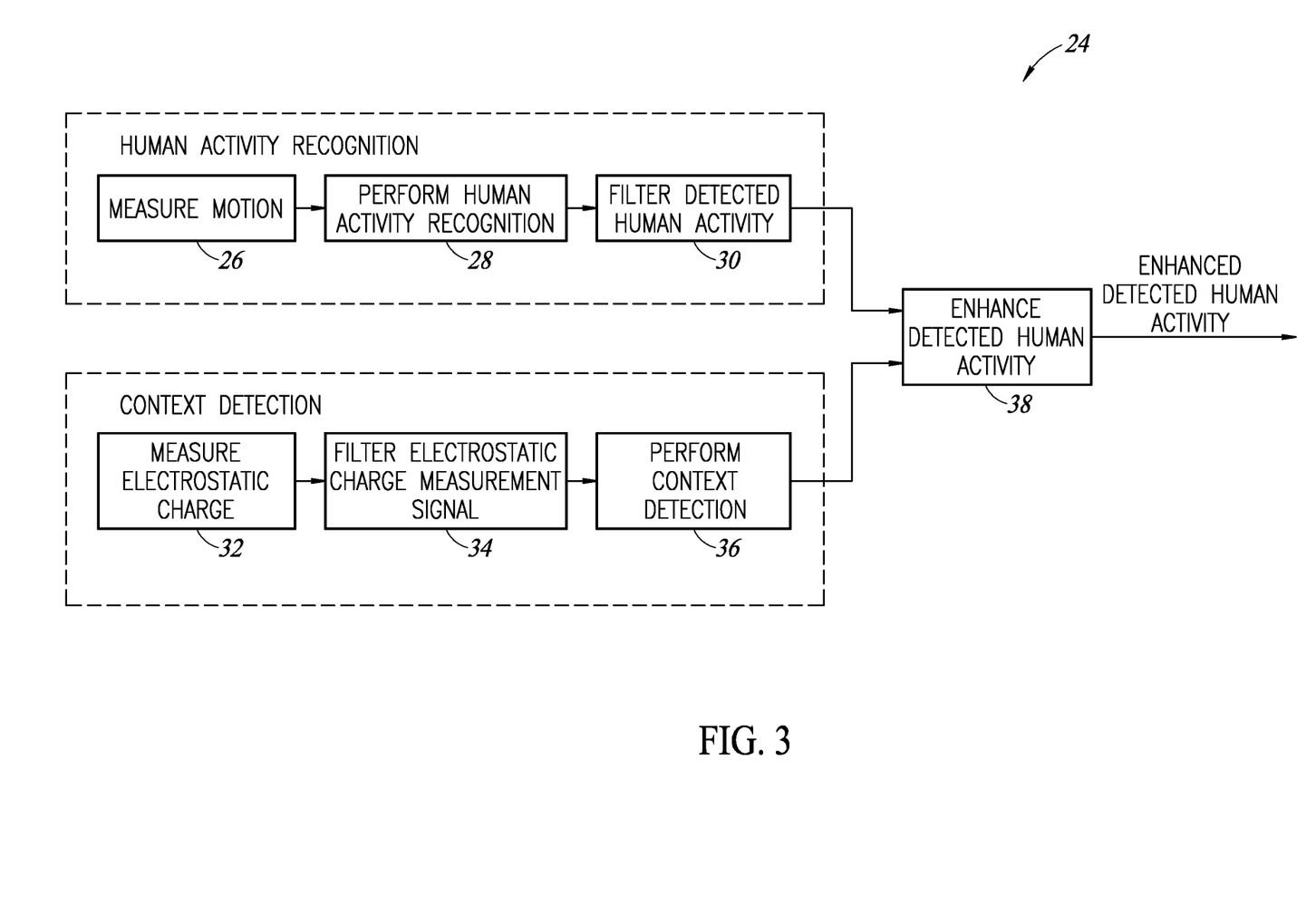
FIG. 3 is a flow diagram of a method of detecting human activity according to an embodiment disclosed herein.

FIG. 3 is a flow diagram of a method 24 of detecting human activity according to an embodiment disclosed herein. The method 24 is performed by the device 10 discussed above. Human activity recognition is performed in blocks 26, 28, and 30; and context detection is performed in blocks 32, 34, and 36.

Turning first to the human activity recognition in blocks 26, 28, and 30, the device 10, more specifically the processing unit 16, performs human activity recognition to classify motion measurements as the stationary state, the walking state, the cycling state, or the driving state. Other types of activities may also be detected.

In block 26, the motion sensor 12 measures motions of the device 10, and generates a motion measurement signal that indicates the measured motions. In one embodiment, the device 10 includes a buffer to store a plurality of motion measurements, and generates a motion measurement signal using the plurality of motion measurements when the buffer is full. As discussed above with respect to FIG. 1, the motion measurements may be acceleration measurements, angular velocity measurements, another type of motion measurement, or a combination thereof.

In block 28, the processing unit 16 performs human activity recognition based on the motion measurement signal generated in block 26. The human activity recognition determines whether a user of the device 10 is in one of the following states: a stationary state, a walking state, a cycling state, and a driving state.

In the stationary state, the user is remaining still. In the walking state, the user is currently walking or running either indoors (e.g., on a treadmill) or outdoors. In the cycling state, the user is currently bicycling either indoors on a stationary bicycle or outdoors. In the driving state, the user is currently driving in a vehicle.

The processing unit 16 classifies motion measurements as the stationary state, the walking state, the cycling state, or the driving state using machine learning techniques, such as a decision tree, a neural network, and a support vector machine. For example, the processing unit 16 computes a set of features to match current motion measurements to motion measurements expected for one of a plurality of pre-defined classes of targeted activities of interest. Such an approach utilizes labeled training data for each of the activities desired to be recognized in order to generate the classifier. Moreover, deep neural network models may also be used and implemented for human activity recognition. Deep neural network models are capable of performing automatic feature learning from the raw sensor data. Statistical models (e.g., Markov models and/or the like) can also be used.

In one embodiment, the processing unit 16 extracts features from the motion measurement signal. For example, the processing unit 16 determines at least one of the following calculations to characterize the motion measurement signal: an energy calculation (e.g., a total energy of the motion measurement signal in a period of time), a variance calculation (e.g., a variance of the motion measurement signal in a period of time), a zero crossing calculation (e.g., a number of times the motion measurement signal crosses zero in a period of time), a peak-to-peak calculation (e.g., a difference between the maximum amplitude and the minimum amplitude of the motion measurement signal in a period of time), a peak count calculation (e.g., a total number of peaks in the motion measurement signal in a period of time), an absolute mean calculation (e.g., an absolute mean of the electrostatic charge measurement signal in a period of time), a maximum calculation (e.g., a maximum of the electrostatic charge measurement signal in a period of time), or a minimum calculation (e.g., a minimum of the motion measurement signal in a period of time). Other types of calculations are also possible. In one embodiment, the features are extracted within a time window of the motion measurement signal. For example, the features may be calculated within a 2.5 second time window. The time window is, for example, defined based on a minimum number of motion measurements to ensure proper human activity recognition.

The processing unit 16 then classifies the motion measurement signal as the stationary state, the walking state, the cycling state, or the driving state based on the extracted features. In one embodiment, a decision tree, such as the one in the following table, is used to classify the motion measurement signal as the stationary state, the walking state, the cycling state, or the driving state. Other machine learning techniques are also possible. In the following decision tree, the motion measurement signal is an acceleration measurement signal along at least one axis.

| Condition | State |
| --- | --- |
| First Peak Count Calculation ≤ First Peak Count Threshold AND<br>First Variance Calculation ≤ First Variance Threshold | Stationary |
| First Peak Count Calculation ≤ First Peak Count Threshold AND<br>First Variance Calculation > First Variance Threshold AND<br>First Zero Crossing Calculation ≤ First Zero Crossing Threshold AND<br>First Minimum Calculation ≤ First Minimum Threshold | Stationary |
| First Peak Count Calculation ≤ First Peak Count Threshold AND<br>First Variance Calculation > First Variance Threshold AND<br>First Zero Crossing Calculation ≤ First Zero Crossing Threshold AND<br>First Minimum Calculation > First Minimum Threshold | Walking |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation ≤ Second Peak Count Threshold | Walking |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation > Second Peak Count Threshold AND<br>Second Variance Calculation ≤ Second Variance Threshold AND<br>Third Peak Count Calculation ≤ Third Peak Count Threshold AND<br>Second Minimum Calculation ≤ Second Minimum Threshold | Stationary |

-continued

| Condition | State |
|---|---|
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation > Second Peak Count Threshold AND<br>Second Variance Calculation ≤ Second Variance Threshold AND<br>Third Peak Count Calculation ≤ Third Peak Count Threshold AND<br>Second Minimum Calculation > Second Minimum Threshold | Walking |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation > Second Peak Count Threshold AND<br>Second Variance Calculation ≤ Second Variance Threshold AND<br>Third Peak Count Calculation > Third Peak Count Threshold AND<br>Third Variance Calculation ≤ Third Variance Threshold | Stationary |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation > Second Peak Count Threshold AND<br>Second Variance Calculation ≤ Second Variance Threshold AND<br>Third Peak Count Calculation > Third Peak Count Threshold AND<br>Third Variance Calculation > Third Variance Threshold AND<br>Third Minimum Calculation ≤ Third Minimum Threshold | Stationary |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation > Second Peak Count Threshold AND<br>Second Variance Calculation ≤ Second Variance Threshold AND<br>Third Peak Count Calculation > Third Peak Count Threshold AND<br>Third Variance Calculation > Third Variance Threshold AND<br>Third Minimum Calculation > Third Minimum Threshold | Walking |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation ≤ Second Zero Crossing Threshold AND<br>Second Peak Count Calculation > Second Peak Count Threshold AND<br>Second Variance Calculation > Second Variance Threshold | Walking |
| First Peak Count Calculation ≤ First Peak Count Threshold AND<br>First Variance Calculation > First Variance Threshold AND<br>First Zero Crossing Calculation > First Zero Crossing Threshold AND<br>Second Zero Crossing Calculation > Second Zero Crossing Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation ≤ Second Peak-To-Peak Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation ≤ Third Zero Crossing Threshold AND<br>Fourth Peak Count Calculation ≤ Fourth Peak Count Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation ≤ Third Zero Crossing Threshold AND<br>Fourth Peak Count Calculation > Fourth Peak Count Threshold AND<br>Fourth Zero Crossing Calculation ≤ Fourth Zero Crossing Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation ≤ Third Zero Crossing Threshold AND<br>Fourth Peak Count Calculation > Fourth Peak Count Threshold AND<br>Fourth Zero Crossing Calculation > Fourth Zero Crossing Threshold AND<br>Fourth Variance Calculation ≤ Fourth Variance Threshold AND<br>Fifth Variance Calculation ≤ Fifth Variance Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation ≤ Third Zero Crossing Threshold AND<br>Fourth Peak Count Calculation > Fourth Peak Count Threshold AND<br>Fourth Zero Crossing Calculation > Fourth Zero Crossing Threshold AND<br>Fourth Variance Calculation ≤ Fourth Variance Threshold AND<br>Fifth Variance Calculation > Fifth Variance Threshold | Driving |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND | Stationary |

-continued

| Condition | State |
|---|---|
| Third Zero Crossing Calculation ≤ Third Zero Crossing Threshold AND<br>Fourth Peak Count Calculation > Fourth Peak Count Threshold AND<br>Fourth Zero Crossing Calculation > Fourth Zero Crossing Threshold AND<br>Fourth Variance Calculation > Fourth Variance Threshold AND<br>Fifth Peak Count Calculation ≤ Fifth Peak Count Threshold | |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation ≤ Third Zero Crossing Threshold AND<br>Fourth Peak Count Calculation > Fourth Peak Count Threshold AND<br>Fourth Zero Crossing Calculation > Fourth Zero Crossing Threshold AND<br>Fourth Variance Calculation > Fourth Variance Threshold AND<br>Fifth Peak Count Calculation > Fifth Peak Count Threshold | Driving |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation ≤ Sixth Variance Threshold AND<br>Seventh Variance Calculation ≤ Seventh Variance Threshold AND<br>Sixth Peak Count Calculation ≤ Sixth Peak Count Threshold AND<br>Third Peak-To-Peak Calculation ≤ Third Peak-To-Peak Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation ≤ Sixth Variance Threshold AND<br>Seventh Variance Calculation ≤ Seventh Variance Threshold AND<br>Sixth Peak Count Calculation ≤ Sixth Peak Count Threshold AND<br>Third Peak-To-Peak Calculation > Third Peak-To-Peak Threshold AND<br>Seventh Peak Count Calculation ≤ Seventh Peak Count Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation ≤ Sixth Variance Threshold AND<br>Seventh Variance Calculation ≤ Seventh Variance Threshold AND<br>Sixth Peak Count Calculation ≤ Sixth Peak Count Threshold AND<br>Third Peak-To-Peak Calculation > Third Peak-To-Peak Threshold AND<br>Seventh Peak Count Calculation > Seventh Peak Count Threshold | Driving |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation ≤ Sixth Variance Threshold AND<br>Seventh Variance Calculation ≤ Seventh Variance Threshold AND<br>Sixth Peak Count Calculation > Sixth Peak Count Threshold | Driving |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation ≤ Sixth Variance Threshold AND<br>Seventh Variance Calculation > Seventh Variance Threshold | Driving |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation > Sixth Variance Threshold AND<br>Eighth Variance Calculation ≤ Eighth Variance Threshold AND<br>Eighth Peak Count Calculation ≤ Eighth Peak Count Threshold AND<br>Ninth Peak Count Calculation ≤ Ninth Peak Count Threshold | Stationary |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation > Sixth Variance Threshold AND<br>Eighth Variance Calculation ≤ Eighth Variance Threshold AND<br>Eighth Peak Count Calculation ≤ Eighth Peak Count Threshold AND<br>Ninth Peak Count Calculation > Ninth Peak Count Threshold AND<br>Fourth Peak-To-Peak Calculation ≤ Fourth Peak-To-Peak Threshold | Driving |
| First Peak Count Calculation > First Peak Count Threshold AND<br>First Peak-To-Peak Calculation ≤ First Peak-To-Peak Threshold AND<br>Second Peak-To-Peak Calculation > Second Peak-To-Peak Threshold AND<br>Third Zero Crossing Calculation > Third Zero Crossing Threshold AND<br>Sixth Variance Calculation > Sixth Variance Threshold AND<br>Eighth Variance Calculation ≤ Eighth Variance Threshold AND<br>Eighth Peak Count Calculation ≤ Eighth Peak Count Threshold AND<br>Ninth Peak Count Calculation > Ninth Peak Count Threshold AND | Stationary |

-continued

| Condition | State |
|---|---|
| Fourth Peak-To-Peak Calculation > Fourth Peak-To-Peak Threshold AND Tenth Peak Count Calculation ≤ Tenth Peak Count | |
| First Peak Count Calculation > First Peak Count Threshold AND First Peak-To-Peak Calculation ≤ First Peak-To-Peak Threshold AND Second Peak-To-Peak Calculation > Second Peak-To-Peak Threshold AND Third Zero Crossing Calculation > Third Zero Crossing Threshold AND Sixth Variance Calculation > Sixth Variance Threshold AND Eighth Variance Calculation ≤ Eighth Variance Threshold AND Eighth Peak Count Calculation ≤ Eighth Peak Count Threshold AND Ninth Peak Count Calculation > Ninth Peak Count Threshold AND Fourth Peak-To-Peak Calculation > Fourth Peak-To-Peak Threshold AND Tenth Peak Count Calculation > Tenth Peak Count | Driving |
| First Peak Count Calculation > First Peak Count Threshold AND First Peak-To-Peak Calculation ≤ First Peak-To-Peak Threshold AND Second Peak-To-Peak Calculation > Second Peak-To-Peak Threshold AND Third Zero Crossing Calculation > Third Zero Crossing Threshold AND Sixth Variance Calculation > Sixth Variance Threshold AND Eighth Variance Calculation ≤ Eighth Variance Threshold AND Eighth Peak Count Calculation > Eighth Peak Count Threshold | Driving |
| First Peak Count Calculation > First Peak Count Threshold AND First Peak-To-Peak Calculation ≤ First Peak-To-Peak Threshold AND Second Peak-To-Peak Calculation > Second Peak-To-Peak Threshold AND Third Zero Crossing Calculation > Third Zero Crossing Threshold AND Sixth Variance Calculation > Sixth Variance Threshold AND Eighth Variance Calculation > Eighth Variance Threshold AND Fifth Zero Crossing Calculation ≤ Fifth Zero Crossing Threshold | Stationary |
| First Peak Count Calculation > First Peak Count Threshold AND First Peak-To-Peak Calculation ≤ First Peak-To-Peak Threshold AND Second Peak-To-Peak Calculation > Second Peak-To-Peak Threshold AND Third Zero Crossing Calculation > Third Zero Crossing Threshold AND Sixth Variance Calculation > Sixth Variance Threshold AND Eighth Variance Calculation > Eighth Variance Threshold AND Fifth Zero Crossing Calculation > Fifth Zero Crossing Threshold | Cycling |
| First Peak Count Calculation > First Peak Count Threshold AND First Peak-To-Peak Calculation > First Peak-To-Peak Threshold AND Eleventh Peak Count Calculation ≤ Eleventh Peak Count Threshold AND Sixth Zero Crossing Calculation ≤ Sixth Zero Crossing Threshold | Stationary |
| First Peak Count Calculation > First Peak Count Threshold AND First Peak-To-Peak Calculation > First Peak-To-Peak Threshold AND Eleventh Peak Count Calculation ≤ Eleventh Peak Count Threshold AND Sixth Zero Crossing Calculation > Sixth Zero Crossing Threshold | Cycling |
| First Peak Count Calculation > First Peak Count Threshold AND First Peak-To-Peak Calculation > First Peak-To-Peak Threshold AND Eleventh Peak Count Calculation > Eleventh Peak Count Threshold | Cycling |

In the decision tree above, the first zero crossing threshold is less than the second zero crossing threshold, the third zero crossing threshold is greater than the fourth zero crossing threshold, and the third zero crossing threshold is less than the fifth zero crossing threshold. The first peak count threshold is greater than the second peak count threshold, the second peak count threshold is less than the third peak count threshold, the first peak count threshold is less than the fourth peak count threshold, the fourth peak count threshold is less than the fifth peak count threshold, the first peak count threshold is less than the sixth peak count threshold, the sixth peak count threshold is greater than the seventh peak count threshold, the first peak count threshold is less than the eighth peak count threshold, the eighth peak count threshold is greater than the ninth peak count threshold, the ninth peak count threshold is less than the tenth peak count threshold, and the first peak count threshold is less than the eleventh peak count threshold. The first variance threshold is less than the second variance threshold, the second variance threshold is greater than the third variance threshold, the fourth variance threshold is greater than the fifth variance threshold, the sixth variance threshold is greater than the seventh variance threshold, and the sixth variance threshold is less than the eighth variance threshold. The first minimum threshold is greater than the second minimum threshold, and the second minimum threshold is less than the third minimum threshold. The first peak-to-peak threshold is greater than the second peak-to-peak threshold, the second peak-to-peak threshold is greater than the third peak-to-peak threshold, and the second peak-to-peak threshold is less than the fourth peak-to-peak threshold.

In block 30, the processing unit 16 filters the classifications of the motion measurement signal in block 28 in order to eliminate or reduce false positives. Stated differently, the processing unit 16 eliminates classifications of the motions measurement signal as the stationary state, the walking state, the cycling state, or the driving state that are likely to be incorrect.

In one embodiment, the processing unit 16 reduces false classifications by maintaining a count value for each possible state (i.e., for each of the stationary state, the walking state, the cycling state, and the driving state). The count value is a total number of times the processing unit 16 classified the motion measurement signal as a particular state (e.g., the stationary state, the walking state, the cycling state, or the driving state). When the total number is equal to or greater than a threshold count value, the processing unit 16 determines that the motion measurement signal is in the state.

It is noted that block 30 may be removed from the method 24 (i.e., not performed) to reduce latency of the human activity recognition.

As will be discussed in further detail below, in block 38, the state detected in block 30 (or block 28 in the case where block 30 is removed) is subsequently enhanced based on context detection results.

Now turning to the context detection in blocks 32, 34, and 36, the device 10, more specifically the processing unit 16, performs context detection to detect whether the device 10 is in an indoor or outdoor environment. The processing unit 16 determines whether the device 10 is an indoor or outdoor environment by detecting an indoor AC power line that provides power to the home or building. The processing unit 16 determines the device 10 is in an indoor environment in response to detecting an indoor AC power line, and determines the device 10 is in an outdoor environment in response to detecting that an indoor AC power line is not present.

In block 32, the electrostatic charge sensor 14 measures an electrostatic charge of a surrounding environment, and generates an electrostatic charge measurement signal that indicates the measured electrostatic charges. In one embodiment, the device 10 includes a buffer to store a plurality of electrostatic charge measurements, and generates an electrostatic charge measurement signal using the plurality of electrostatic charge measurements when the buffer is full. The electrostatic charge sensor 14 may measure electrostatic charge continuously or periodically (e.g., every 10 seconds).

In block 34, the processing unit 16 filters the electrostatic charge measurement signal to remove unnecessary electrostatic charge measurements. In one embodiment, a high pass filter is applied to the electrostatic charge measurement signal. A cutoff frequency of the high pass filter is selected based on the frequency of the AC power line being detected. For example, the cutoff frequency may be set to 40 hertz when a 50 hertz and a 60 hertz AC power line is being detected. Other types of filters, such as a low pass filter and band pass filter, may also be applied to the electrostatic charge measurement signal.

It is noted that block 34 may be removed from the method 24 (i.e., not performed).

In block 36, the processing unit 16 performs context detection based on the filtered electrostatic charge signal generated in block 34 (or the electrostatic charge signal generated in block 32 in the case where block 34 is removed). As mentioned above, the context detection detects whether the device 10 is in an indoor or outdoor environment. Context detection is performed using either a frequency approach or a time domain approach.

In the frequency approach, the processing unit 16 converts the electrostatic measurement signal to the frequency domain by applying, for example, a fast Fourier transform to the electrostatic measurements. Other techniques for converting the electrostatic measurements to the frequency domain may also be used.

The processing unit 16 then performs tone detection to detect whether electrostatic charge signal includes a peak corresponding to a frequency of an indoor AC power line. When the device 10 is indoors and near an AC power line, the processing unit 16 detects an electrostatic charge with a frequency corresponding to a frequency of the AC power line. For example, in a case where the device 10 is in a house with an AC power line having a frequency of 60 hertz, the electrostatic charge sensor 14 detects an electrostatic charge peak or tone at 60 hertz. Conversely, in a case where the device 10 is outdoors and is not in proximity to an AC power line, the processing unit 16 does not detect an electrostatic charge peak at 60 hertz, or detects an electrostatic charge peak at 60 hertz that is substantially smaller than the 60 hertz electrostatic charge peak detected in the case where the device 10 is in the house with the AC power line having a frequency of 60 hertz.

Figure 4:
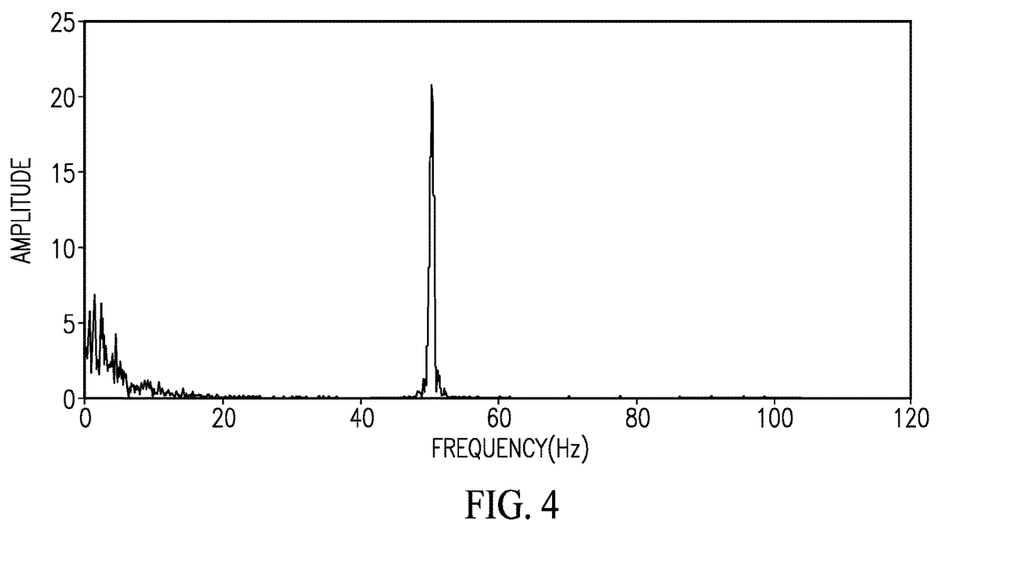
FIG. 4 is an electrostatic charge measurement signal in a case where a device is indoors according to an embodiment disclosed herein.
Figure 5:
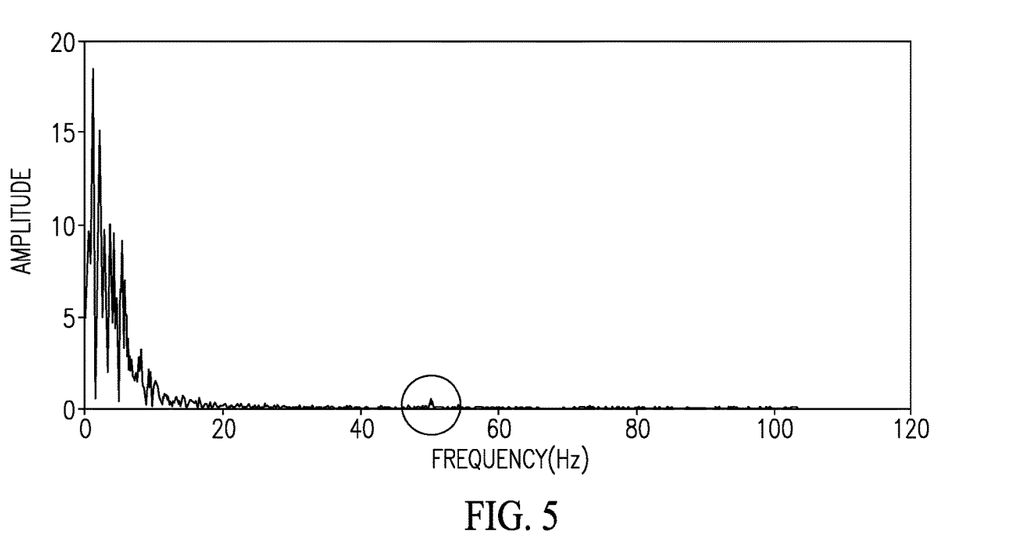
FIG. 5 is an electrostatic charge measurement signal in a case where a device is outdoors according to an embodiment disclosed herein.

For example, FIG. 4 is an electrostatic charge measurement signal in a case where the device 10 is indoors according to an embodiment disclosed herein, and FIG. 5 is an electrostatic charge measurement signal in a case where the device 10 is outdoors according to an embodiment disclosed herein. In the example shown in FIG. 4, the indoor AC power line has a frequency of 50 hertz. Detection of AC power lines with other frequencies (e.g., 60 hertz) is also possible.

In FIGS. 4 and 5, the vertical axes are amplitudes of the electrostatic charge measurement signals, and the horizontal axes are frequency axes. The amplitudes are outputs from an ADC, and the frequency axes are in hertz. Other amplitude and frequency units are also possible.

As can be seen in FIG. 4, the electrostatic charge sensor 14 detects an electrostatic charge peak or tone at approximately 50 hertz. Thus, in this example, the device 10 is in the presence of a 50 hertz AC power line, and the processing unit 16 determines the device 10 is indoors. In contrast, in FIG. 5, the electrostatic charge sensor 14 detects an electrostatic charge peak at approximately 50 hertz (in the encircled area in FIG. 5) that is substantially smaller than the 50 hertz electrostatic charge peak detected in FIG. 4. Thus, in this example, the device 10 is not in the presence of a 50 hertz AC power line, and the processing unit 16 determines the device 10 is outdoors.

Accordingly, in the frequency approach, the processing unit 16 determines whether the device 10 is indoors or outdoors based on whether or not the electrostatic charge signal includes a peak at a frequency of an indoor AC power line.

In the time domain approach, the processing unit 16 classifies electrostatic charge measurements in the time domain as an indoor state or an outdoor state using either deterministic or machine learning techniques, such as a decision tree, a neural network, and a support vector machine. For example, similar to the human activity recognition in block 28, the processing unit 16 computes a set of features to match current electrostatic charge measurements to electrostatic charge measurements expected for the indoor state and the outdoor state. Such an approach utilizes labeled training data for each of the indoor state and the outdoor state in order to generate the classifier. Moreover, deep neural network models may also be used and implemented for indoor and outdoor detection. Deep neural network models are capable of performing automatic feature learning from the raw sensor data and out-perform models fit on hand-crafted domain-specific features. Statistical models (e.g., Markov models and/or the like) can also be used.

In one embodiment, the processing unit 16 extracts features from the electrostatic charge measurement signal. For example, the processing unit 16 determines at least one of the following calculations, which were also discussed above with respect to block 28, to characterize the electrostatic charge measurement signal: an energy calculation, a variance calculation, a zero crossing calculation, a peak-to-peak calculation, a peak count calculation, an absolute mean calculation, a maximum calculation, or a minimum calculation. Other types of calculations are also possible. In one embodiment, the features are extracted within a time window of the electrostatic charge measurement signal. For example, the features may be calculated within a 2.5 second time window. The time window is, for example, defined based on a minimum number of electrostatic charge measurements to ensure proper context detection.

The processing unit 16 then classifies the electrostatic charge measurement signal as the indoor state or the outdoor state based on the extracted features. In one embodiment, a decision tree, such as the one in the following table, is used to classify the electrostatic charge measurement signal as the indoor state or the outdoor state. Other machine learning techniques are also possible.

| Condition | State |
| --- | --- |
| First Variance Calculation ≤ First Variance Threshold AND Zero Crossing Calculation ≤ Zero Crossing Threshold | Outdoor |
| First Variance Calculation ≤ First Variance Threshold AND Zero Crossing Calculation > Zero Crossing Threshold AND Peak Count Calculation ≤ Peak Count Threshold AND Second Variance Calculation ≤ Second Variance Threshold | Outdoor |
| First Variance Calculation ≤ First Variance Threshold AND Zero Crossing Calculation > Zero Crossing Threshold AND Peak Count Calculation ≤ Peak Count Threshold AND Second Variance Calculation > Second Variance Threshold | Indoor |
| First Variance Calculation ≤ First Variance Threshold AND Zero Crossing Calculation > Zero Crossing Threshold AND Peak Count Calculation > Peak Count Threshold AND Peak-To-Peak Calculation ≤ Peak-To-Peak Threshold | Indoor |
| First Variance Calculation ≤ First Variance Threshold AND Zero Crossing Calculation > Zero Crossing Threshold AND Peak Count Calculation > Peak Count Threshold AND Peak-To-Peak Calculation > Peak-To-Peak Threshold | Outdoor |
| First Variance Calculation > First Variance Threshold AND | Indoor |

In the decision tree above, the first variance threshold is greater than the second variance threshold.

In block 38, the state detected in block 30 (or block 28 in the case where block 30 is removed) is enhanced based on the context detected in block 36. Namely, in block 38, the stationary state, the walking state, the cycling state, or the driving state determined in block 30 is refined based on whether the device 10 is determined to be indoors or outdoors in block 36.

In one embodiment, in block 38, the processing unit 16 validates the human activity detected in block 30 (or block 28 in the case where block 30 is removed) by rejecting false state detections (i.e., incorrectly detected states). The processing unit 16 detects false state detections based on whether the device 10 is determined to be indoors or outdoors. In the event the processing unit 16 determines a user of the device 10 is in the driving state and determines that the device 10 is indoors, the processing unit 16 determines that the detection of the driving state is a false detection as it is highly unlikely a user is driving a vehicle indoors. The processing unit 16 then switches the driving state to, for example, the stationary state; and outputs the stationary state as the enhanced detected human activity. Conversely, in the event the processing unit 16 determines a user of the device 10 is in the driving state and determines that the device 10 is outdoors, the processing unit 16 determines that the detection of the driving state is a true detection, and outputs the driving state as the enhanced detected human activity.

In one embodiment, in block 38, the processing unit 16 refines or adjusts the state detected in block 30 to a new classification. In the event the processing unit 16 determines a user of the device 10 is in the walking state and determines that the device 10 is indoors, the processing unit 16 switches the walking state to an indoor walking state that indicates the user is walking or running indoors, and outputs the indoor walking state as the enhanced detected human activity. In the event the processing unit 16 determines a user of the device 10 is in the walking state and determines that the device 10 is outdoors, the processing unit 16 switches the walking state to an outdoor walking state that indicates the user is walking or running outside, and outputs the outdoor walking state as the enhanced detected human activity. In the event the processing unit 16 determines a user of the device 10 is in the cycling state and determines that the device 10 is indoors, the processing unit 16 switches the cycling state to a stationary bicycle state that indicates the user is cycling on a stationary bicycle, and outputs the stationary bicycle state as the enhanced detected human activity. In the event the processing unit 16 determines a user of the device 10 is in the cycling state and determines that the device 10 is outdoors, the processing unit 16 switches the cycling state to an outdoor cycling state that indicates the user is cycling outside, and outputs the outdoor cycling state as the enhanced detected human activity. In this embodiment, motion measurements may be classified as the stationary state, the indoor walking state, the outdoor walking state, the stationary bicycle state, the outdoor cycling state, or the driving state.

In the embodiment shown in FIG. 3, human activity recognition and context detection are performed in parallel with each other, and the detected human activity and the detected context are combined to generate an enhanced detected human activity. Human activity recognition and context detection may also be performed in series. In one embodiment, human activity recognition is performed subsequent to context detection, and human activity recognition is adjusted based on the detected context. In the event the device 10 is determined to be indoors during context detection, human activity recognition is set to detect indoor states and to not detect outdoor states. For example, in the case where machine learning techniques are used for human activity recognition, indoor training data is loaded and used for classification of motion measurements in block 28 in order to detect the stationary state, the indoor walking state, and the stationary bicycle state. Conversely, in the event the device 10 is determined to be outdoors during context detection, human activity recognition is set to detect outdoor states and to not detect indoor states. For example, in the case where machine learning techniques are used for human activity recognition, outdoor training data is loaded and used for classification of motion measurements in block 28 in order to detect the stationary state, the outdoor walking state, the outdoor cycling state, and the driving state.

In the embodiment shown in FIG. 3, human activity recognition and context detection are performed separately. For example, the human activity recognition in block 28 is performed using a first decision tree, and the context detection in block 36 is performed using a second, separate decision tree. In another embodiment, the human activity recognition and the context detection are combined, and a single decision tree is used to detect whether a user of the device 10 is in the stationary state, the indoor walking state, the outdoor walking state, the cycling state, the driving state, or the stationary bicycle state.

The method 24 discussed above may be implemented as a software library included in and executed by a microcontroller (e.g., the processing unit 16) or a communication module (e.g., a Bluetooth Low Energy (BLE) module) of the device 10. The method 24 may also be implemented as hardware within, for example, a sensor device (e.g., a combination sensor that includes the motion sensor 12 and the electrostatic charge sensor 14) of the device 10. In this case, the microcontroller (e.g., the processing unit 16) may be removed from the device 10.

The various embodiments disclosed herein provide a device with enhanced human activity recognition. The device detects a human activity and whether the device is in an indoor or outdoor environment, and enhances the detected human activity based on whether the device is in the indoor or outdoor environment. In contrast to audio-based solutions which utilize microphones to detect an indoor and outdoor environment, the device disclosed herein utilizes one or more electrostatic charge sensors to detect an indoor and outdoor environment. The device consumes significantly less power compared to current audio-based solutions. For example, microphones in audio-based solutions typically consume between 120 and 700 micro amps, whereas electrostatic charge sensors typically consume between 10 and 20 micro amps.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. A device, comprising:
   a motion sensor configured to generate a motion measurement of the device;
   an electrostatic charge sensor configured to generate an electrostatic charge measurement of the device; and
   a processing unit configured to:
   perform context detection to detect the device is indoors or outdoors based on the electrostatic charge measurement;
   perform, subsequent to the device being determined to be indoors based on the electrostatic charge measurement, first human activity recognition to detect a first activity state of a user of the device selected from a plurality of indoor states based on the motion measurement, the first human activity recognition being performed without outdoor state detection;
   perform, subsequent to the device being determined to be outdoors based on the electrostatic charge measurement, second human activity recognition to detect a second activity state of the user of the device selected from a plurality of outdoor states based on the motion measurement, the second human activity recognition being performed without indoor state detection; and
   output the first activity state or the second activity state.

2. The device of claim 1 wherein the processing unit detects the device is indoors in a case where the electrostatic charge measurement includes a first peak at a frequency corresponding to an alternating current (AC) power line.

3. The device of claim 2 wherein the processing unit detects the device is outdoors in a case where the electrostatic charge measurement does not include a peak at the frequency corresponding to the AC power line, or the electrostatic charge measurement includes a second peak, which is smaller than the first peak, at the frequency corresponding to the AC power line.

4. The device of claim 1 wherein the processing unit is configured to determine at least one feature of the electrostatic charge measurement, and detect whether the device is indoors or outdoors based on the at least one feature.

5. The device of claim 4 wherein the at least one feature includes at least one of an energy calculation, a variance calculation, a zero crossing calculation, a peak-to-peak calculation, a peak count calculation, an absolute mean calculation, a maximum calculation, or a minimum calculation.

6. The device of claim 1 wherein the electrostatic charge sensor includes a single electrode.

7. The device of claim 1 wherein the electrostatic charge sensor includes a plurality of electrodes.

8. The device of claim 1 wherein the processing unit is configured to:
   determine a first peak of the electrostatic charge measurement;
   detect the device is indoors in a case where the first peak corresponds to an alternating current (AC) power line;
   determine a second peak of the electrostatic charge measurement; and
   detect the device is outdoors in a case where the second peak corresponds to the AC power line and is smaller than the first peak.

9. The device of claim 1 wherein
   the plurality of indoor states includes a stationary state that indicates the user is remaining still, an indoor walking state that indicates the user is walking indoors, and a stationary bicycle state that indicates the user is cycling on a stationary bicycle, and
   the plurality of outdoor states includes an outdoor walking state that indicates the user is walking outside, an outdoor cycling state that indicates the user is cycling outdoors, and a driving state that indicates the user is driving a vehicle.

10. The device of claim 1 wherein the processing unit is configured to:
    count a first total number of times the first activity state has been determined;
    output the first activity state in response to the first total number being equal to or greater than a first threshold count value;
    count a second total number of times the second activity state has been determined;
    output the second activity state in response to the second total number being equal to or greater than a second threshold count value.

11. The device of claim 1 wherein the processing unit is configured to:
    filter the electrostatic charge measurement with a high pass filter, the device being determined to be indoors or outdoors based on the filtered electrostatic charge measurement.

12. A device, comprising:
    a motion sensor configured to generate a motion measurement of the device;
    an electrostatic charge sensor configured to generate an electrostatic charge measurement of the device; and
    a processing unit configured to:
    perform human activity recognition to detect a driving state of a user of the device based on the motion measurement, the driving state indicating the user is driving a vehicle;
    perform context detection to detect the device is indoors or outdoors based on the electrostatic charge measurement;
    detect a valid detection of the driving state determined based on the motion measurement in response to the device being determined to be outdoors based on the electrostatic charge measurement;

detect a false detection of the driving state determined based on the motion measurement in response to the device being determined to be indoors based on the electrostatic charge measurement;

output the driving state in response to the valid detection of the driving state determined based on the motion measurement being detected.

13. The device of claim 12 wherein the processing unit detects the device is indoors in a case where the electrostatic charge measurement includes a first peak at a frequency corresponding to an alternating current (AC) power line, and detects the device is outdoors in a case where the electrostatic charge measurement does not include a peak at the frequency corresponding to the AC power line, or the electrostatic charge measurement includes a second peak, which is smaller than the first peak, at the frequency corresponding to the AC power line.

14. The device of claim 12 wherein the processing unit is configured to determine at least one feature of the electrostatic charge measurement, and detect whether the device is indoors or outdoors based on the at least one feature.

15. The device of claim 14 wherein the at least one feature includes at least one of an energy calculation, a variance calculation, a zero crossing calculation, a peak-to-peak calculation, a peak count calculation, an absolute mean calculation, a maximum calculation, or a minimum calculation.

16. The device of claim 12 wherein the processing unit is configured to, in response to the false detection of the driving state determined based on the motion measurement being detected, switch the driving state to another state different from the driving state, and output the another state.

17. A device, comprising:
a motion sensor configured to generate a motion measurement of the device;
an electrostatic charge sensor configured to generate an electrostatic charge measurement of the device; and
a processing unit configured to:
determine a walking state of a user of the device based on the motion measurement, the walking state indicating the user is walking;
determine a cycling state of the user of the device based on the motion measurement, the cycling state indicating the user is cycling;
determine the device is indoors or outdoors based on the electrostatic charge measurement;
in case the walking state is determined,
switch the walking state determined based on the motion measurement to an indoor walking state that indicates the user is walking indoors in response to the device being determined to be indoors based on the electrostatic charge measurement, and output the indoor walking state, and
switch the walking state to an outdoor walking state determined based on the motion measurement that indicates the user is walking outdoors in response to the device being determined to be outdoors, and output the outdoor walking state based on the electrostatic charge measurement; and
in case the cycling state is determined,
switch the cycling state determined based on the motion measurement to a stationary bicycle state that indicates the user is cycling on a stationary bicycle in response to the device being determined to be indoors based on the electrostatic charge measurement, and output the stationary bicycle state, and
switch the cycling state determined based on the motion measurement to an outdoor cycling state that indicates the user is cycling outdoors in response to the device being determined to be outdoors based on the electrostatic charge measurement, and output the outdoor cycling state.

18. The device of claim 17 wherein the processing unit determines the device is indoors in a case where the electrostatic charge measurement incudes a first peak at a frequency corresponding to an alternating current (AC) power line, and determines the device is outdoors in a case where the electrostatic charge measurement does not include a peak at the frequency corresponding to the AC power line, or the electrostatic charge measurement includes a second peak, which is smaller than the first peak, at the frequency corresponding to the AC power line.

* * * * *